United States Patent [19]
Yipp

[11] Patent Number: 6,076,535
[45] Date of Patent: Jun. 20, 2000

[54] DENTAL FLOSSER

[76] Inventor: Anthony F. Yipp, 2214 S. Broadway, Santa Ana, Calif. 92707

[21] Appl. No.: 08/999,985

[22] Filed: Dec. 17, 1997

Related U.S. Application Data

[63] Continuation-in-part of application No. 08/789,080, Jan. 27, 1997, abandoned, which is a continuation-in-part of application No. 08/695,557, Aug. 12, 1996, abandoned.

[51] Int. Cl.[7] .................................................. A61C 15/04
[52] U.S. Cl. ............................................. 132/324; 225/80
[58] Field of Search ..................... 132/323, 324, 132/325, 326, 327; 225/77, 80, 91

[56] References Cited

U.S. PATENT DOCUMENTS

| | | | |
|---|---|---|---|
| 1,102,401 | 7/1914 | Gamble | 132/325 |
| 1,161,043 | 11/1915 | Gallas | 132/325 |
| 1,174,016 | 2/1916 | Kenyon | 132/325 |
| 1,219,986 | 3/1917 | Muchow | 132/325 |
| 1,468,942 | 9/1923 | Gamble | 132/324 |
| 1,667,134 | 4/1928 | Sherwood | 132/323 |
| 1,952,358 | 3/1934 | Bohm | 132/326 |
| 2,052,520 | 8/1936 | Sonnenberg | 132/324 |
| 2,163,500 | 6/1939 | Shepard | 132/326 |
| 2,467,221 | 4/1949 | Pastl | 132/326 |
| 2,517,806 | 8/1950 | Streiler | 132/323 |
| 2,853,082 | 9/1958 | Nelson | 132/325 |
| 3,789,859 | 2/1974 | Chambers | 132/326 |
| 4,206,774 | 6/1980 | Griparis | 132/326 |
| 4,788,990 | 12/1988 | Wisegerber | 132/324 |
| 5,573,021 | 11/1996 | Grofcisk et al. | 132/324 |

FOREIGN PATENT DOCUMENTS

| 2272161 | 5/1994 | United Kingdom | 132/323 |
|---|---|---|---|

*Primary Examiner*—Todd E. Manahan
*Assistant Examiner*—Eduardo C. Robert
*Attorney, Agent, or Firm*—John J. Connors; Connors & Assoc.

[57] ABSTRACT

A dental flosser 10 includes a handle 12 having a hollow interior 14 adapted to hold a supply of dental floss 26. The handle 12 has an open end providing access to the hollow interior 14, and a cap has one end is connected to this open end of the handle 12. Another end of the cap includes a pair of fingers which are spaced apart. Each finger has a opening therein near a distal end thereof. The end of the cap connected to the handle 12 has a guideway which permits floss 26 to pass from the hollow interior 14 and be threaded through the openings in the fingers. A post 42 is attached to the cap member 16 between the fingers elements and the one end of the cap member 16. This post 42 includes a guideway 40 for the floss 26 and a blade 50 for cutting the floss. The post 42 has an underside which intersects the cap member 16 at an acute angle to provide notch structures 54 and 56.

20 Claims, 8 Drawing Sheets

DENTAL FLOSSER

RELATED PATENT APPLICATIONS

This application is a continuation-in-part application of U.S. Ser. No. 08/789,080, entitled "Dental Flosser," filed Jan. 27, 1997, now abandoned which in turn is a continuation-in-part application of U.S. Ser. No. 08/695,557, entitled "Dental Flosser," filed Aug. 12, 1996, now abandoned. These related applications are incorporated herein by reference and made a part of this application.

BACKGROUND OF THE INVENTION

1. Field of the Invention

This invention relates to a novel flosser for flossing teeth, and a roll of dental floss constructed to function with this novel flosser.

2. Background Discussion

Dentists recommend flossing teeth as a way to keep teeth free of plac to prevent gum disease. The problem with flossing is that it is difficult to do. Many people find it necessary to employ a tool to assist them in flossing. It would be desirable when the floss is used up to quickly disassemble the flosser and add a new roll of floss. It is the objective of this invention to provide a low cost, simple to use and effective dental flosser which contains a supply of dental floss that is particular designed to function with the flosser and can be replaced when used up.

SUMMARY OF THE INVENTION

This invention has several features, no single one of which is solely responsible for its desirable attributes. Without limiting the scope of this invention as expressed by the claims which follow, its more prominent features will now be discussed briefly. After considering this discussion, and particularly after reading the section entitled, "DETAILED DESCRIPTION OF THE PREFERRED EMBODIMENT," one will understand how the features of this invention provide its benefits, which include low cost manufacture, convenience in accessing a self contained floss supply, and ease of stringing floss through the flosser, and firmness in anchoring of the floss so that it remains in tension during use of the flosser to clean teeth.

The first feature of the dental flosser of this invention is that it includes a handle having a hollow interior adapted to hold a supply of dental floss. The handle has an open end providing access to the hollow interior. Thus, the handle may be refilled with a supply of dental floss as needed.

The second feature is a cap member having one end which is connected to the open end of the handle and another end including a pair of finger elements. The cap member is disconnected from the handle to allow floss to be placed in the hollow interior of the handle.

The third feature is that the finger elements are spaced apart a predetermine distance suitable for flossing. Typically, this ranges from 10 to 30 centimeters. Each finger element has a proximal end and distal end and an opening therein near the distal end thereof. The end of the cap member connected to the handle has a guideway therein which permits floss to pass from the hollow interior and be treaded through the holes in the fingers. Preferably, the finger elements join together at proximal ends thereof to form a fork or generally V-shaped configuration, and in each finger element there is an intermediate hole between the proximal and distal ends of the finger elements. The user first passes the floss through an intermediate opening in one of the finger elements, next the user passes the floss through the distal openings in this one finger element, then stretching it across the space between the distal ends of the fingers, then passing it through the distal opening in the other finger element, and finally passing it through the intermediate opening in this other finger element. The floss is stretched tight across the space between the distal ends of the finger elements, creating tension in the floss.

The fourth feature is a post near the handle for anchoring the floss in position in tension between the distal ends of the finger elements. Preferably, the post is on the cap adjacent the proximal ends of the finger elements. There is a passageway on the post for the floss. This guideway preferably has a generally Y-shaped configuration. This enables the flosser to be conveniently used by either left or right handed persons. The post has an underside wall which intersects the cap member at an acute angle to provide a notch structure. This enables the user to wrap the floss around the post, with a portion of the floss is wedged into the notch structure to anchor it in position in tension. Preferably, the post has notch structures at its opposite ends. There is a blade on the cap member for cutting the floss, preferably on the post.

The fifth feature is that the post has a substantially C-shaped configuration, with a base. The notches are adjacent the base. This base has a proximal end and a distal end with a raised arm at each end. Each raised arm has a slot therein, and the slots are offset relative to each other. These slots serve as a passageway for the floss.

The sixth feature is that the blade is attached to the post near the distal end of the base. Preferably, the blade is next to the slot in the distal end of the base and spaced from the proximal end of the base. The blade has a cutting edge facing the proximal end of the base. The raised arm at the distal end of the base has a lip extending inward towards the proximal end of the base, and the blade is seated on the post to extend between the lip and the base and to one side of the slot in the arm at the distal end of the base. The cutting edge of the blade is orientated lengthwise and extending between said base and lip, and the blade preferably is substantially straight.

The seventh feature is that there is a ramp having a slanted top surface position on the base between the proximal and distal ends of the base. A hook-type blade is mounted on the top surface of the ramp. The ramp has a distal end and a proximal end and the distal end is elevated relative to the proximal end.

The eighth feature is that in one preferred embodiment the post has a unique configuration which makes it easier to thread the floss through the post and cut it. This uniquely configured post has (a) a base of a predetermined length with a forward end near the pair of finger elements and a rear end near the handle and (b) a top plate having a length substantially equal to the predetermined length of the base and overlying the base so that said base and top plate are substantially co-extensive along their respective lengths. The top plate has a forward end near the pair of finger elements and a rear end near the handle. A connecting member connects the forward ends of the base and top plate and spaces the base and top plate into a substantially parallel orientation with respect to each other and provides an open section between the rear ends of the base and top plate. The blade for cutting the floss is disposed between the base and top plate.

The ninth feature is a novel roll of floss which is specially constructed to be used with the flosser of this invention. In accordance with this feature of the invention, the floss is in the form of an elongated, cylindrically shaped roll which has a hollow, open core with an end of the floss extending from the open core. It is this end which extends from the handle and is threaded through the opening in the finger elements.

DESCRIPTION OF THE DRAWING

The preferred embodiment of this invention, illustrating all its features, will now be discussed in detail. This embodiment depicts the novel and non-obvious dental flosser of this invention as shown in the accompanying drawing, which is for illustrative purposes only. This drawing includes the following figures (FIGS.), with like numerals indicating like parts:

FIG. 1a is a plan view of the cap member of the first embodiment of the dental flosser of this invention.

FIG. 1b is a cross-sectional view of the handle of the dental flosser shown in FIG. 1a.

FIG. 1c is a front plan view, partially in cross-section, showing the assembly of the cap member shown in FIG. 1 and handle, with dental floss contained in the handle and extending from the open end of the handle and passing through a guideway in the cap member.

FIG. 1d is a top plan view of the dental flosser shown in FIG. 1.

FIG. 1e is a bottom plan view of the first embodiment of the dental flosser of this invention.

FIG. 2 is a plan view of the backside of the first embodiment of the dental flosser of this invention.

FIG. 15b is enlarged, fragmentary side view taken along line 15b of FIG. 15a.

DETAILED DESCRIPTION OF THE PREFERRED EMBODIMENTS

The first embodiment of this invention, the dental flosser 10, as shown in FIGS. 1a through 1e, FIG. 2, and FIG. 4, includes a handle 12 having a hollow interior 14 (FIG. 1b) and a cap member 16 which is removably attached to the handle. Both the cap member 16 and handle 12 are preferably made out of a polymeric material such as polyethylene and are injection molded. The handle 12 has a generally cylindrical configuration, with one end 18 closed and an opposed end 20 open, with threads 22 (FIG. 1b) on the interior wall. A roll 24 (FIG. 1c) of floss 26 in the form of a cylinder is inserted into the hollow interior 14 of the handle 12, with one end 26a of the floss 26 passing through the open end of the handle 12.

Figures 1A, 1B, 1C, 1D, 1E, 2:
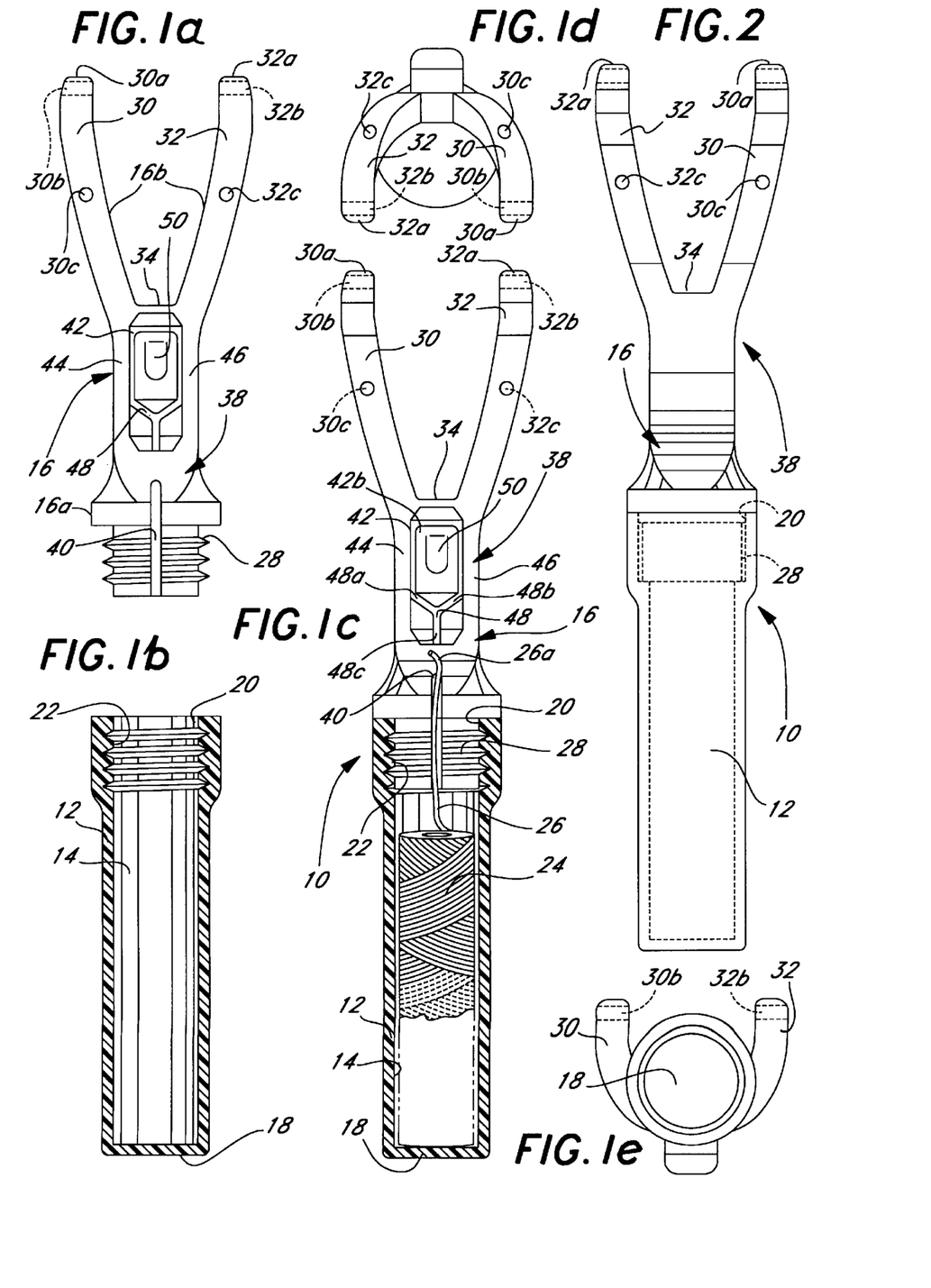

The cap member 16 has at its proximal end 16a a threaded connector 28 which enables the cap member 16 to be removably attached to the handle 12 by threading the connector end into the corresponding threads 22 in the interior 14 of the handle 12. At the distal end 16b of the cap member 16 are a pair of finger elements 30 and 32 which merge at a common junction 34. The distal ends 30a and 32a, respectively, of the finger elements 30 and 32 are spaced apart approximately from 10 to 30 centimeters, and in the sides of these ends 30 and 32 are openings 30b and 32b which are aligned. There are also intermediate openings 30c and 32c, respectively, in the tops of the finger elements 30 and 32, about midway between the ends 30a and 32a of the finger elements and the common junction 34. The ends 30a and 32a of the finger elements 30 and 32 each have smooth and rounded surfaces, enabling these ends to be used for massaging the user's gums. A neck portion 38 connects the finger elements to the connector 28, and an elongated slot 40 serves as a passageway for the floss end 26a exiting the open end 20 of the handle 12. Mounted on the neck portion 38 is a post 42 about which the floss 26 is wrapped after threading the floss through the openings 30c, 30b, 32b, and 32c in the fingers 30 and 32.

Figures 3, 4:
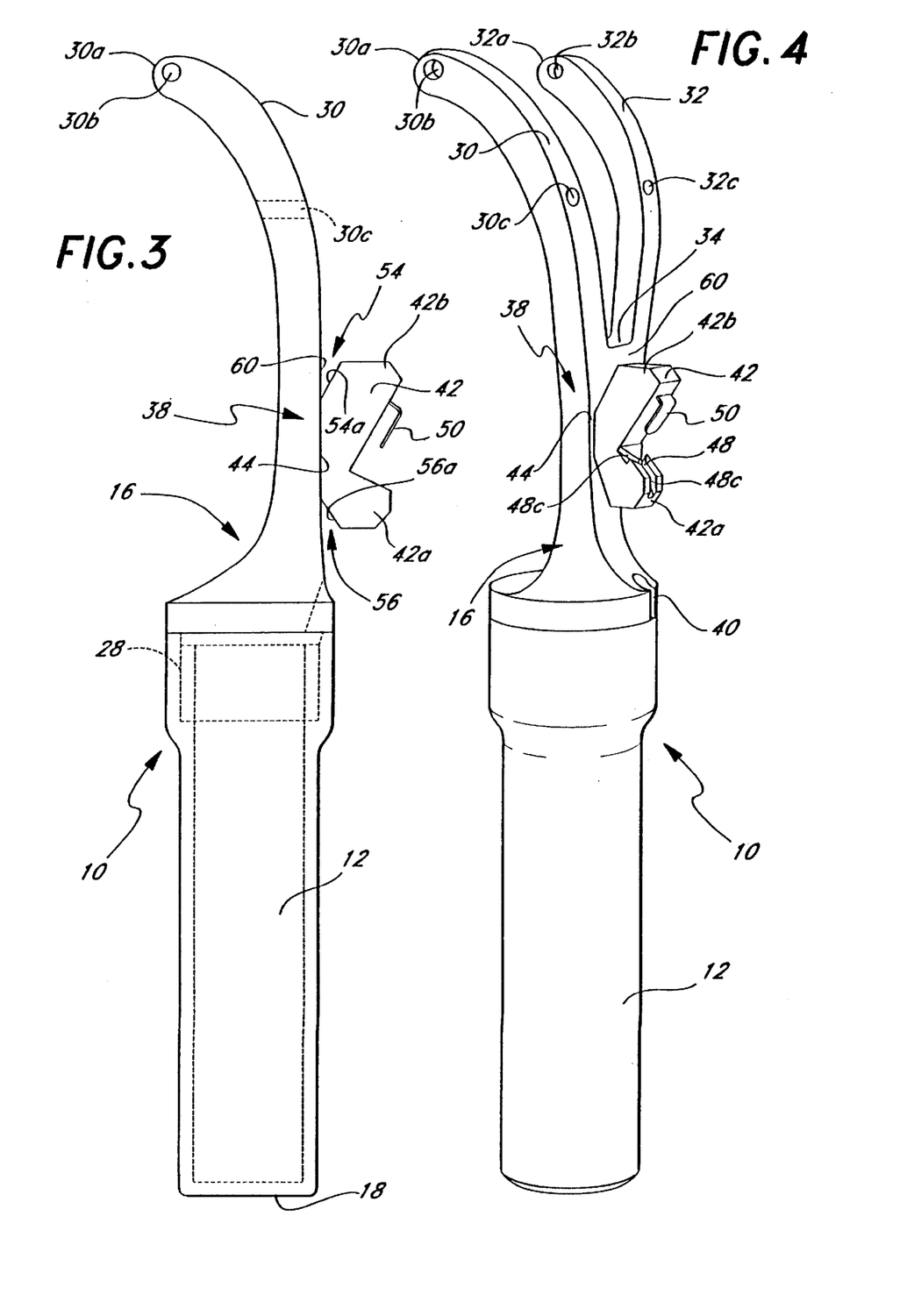
FIG. 3 is a side elevation view of the first embodiment of the dental flosser of this invention.
FIG. 4 is a perspective view of the first embodiment of the dental flosser of this invention.
Figure 5:
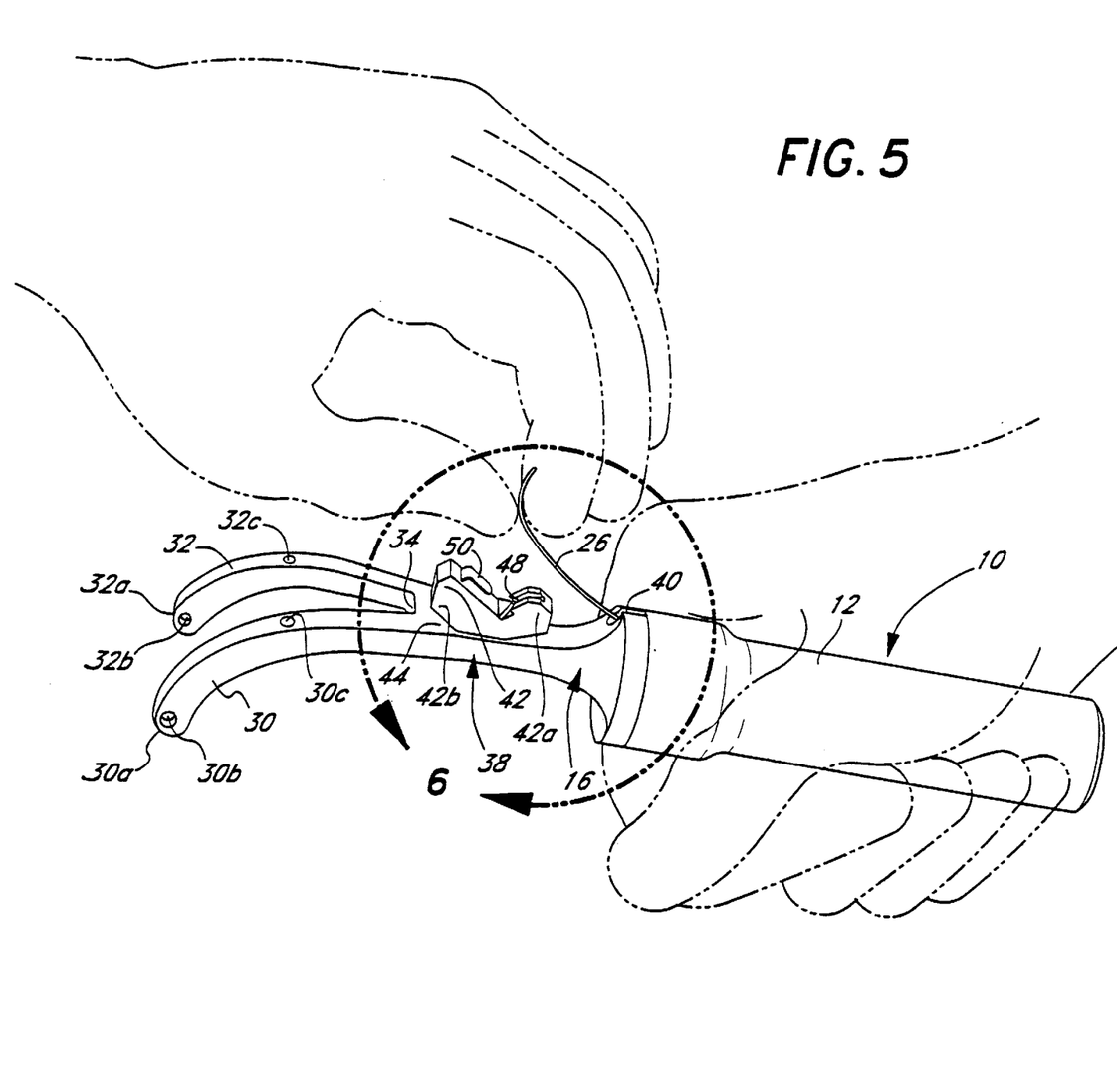
FIG. 5 is a perspective view showing a user holding the handle with one hand and with the other hand commencing threading of the floss.
Figures 6, 7, 8:
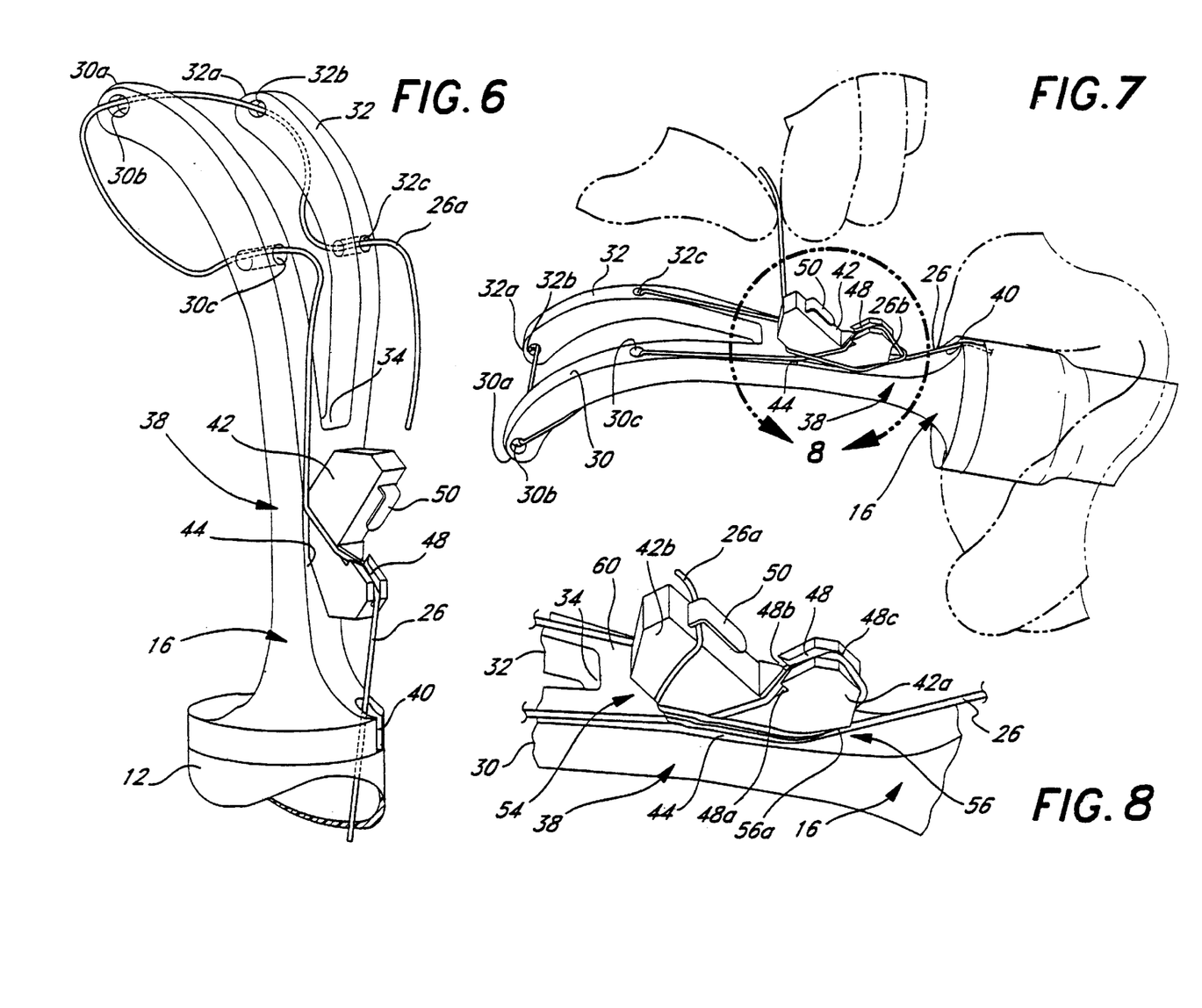
FIG. 6 is a perspective view of the cap member showing the floss partially threaded through openings in the fingers of the cap member.
FIG. 7 is a perspective view showing the floss threaded about the a post on the cap member shown in FIG. 1.
FIG. 8 is an enlarged perspective view showing the floss wrapped about the post.
Figure 9:
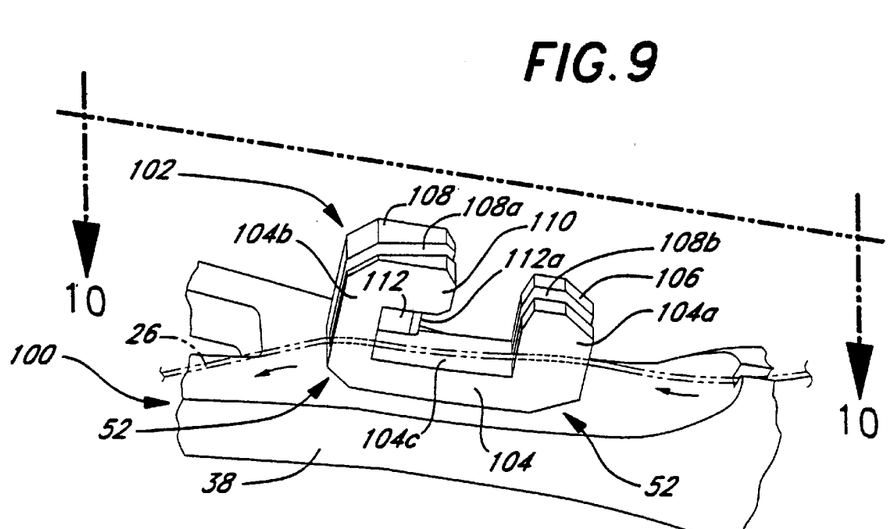
FIG. 9 is an enlarged, fragmentary perspective view of a second embodiment of this invention.
Figure 10:
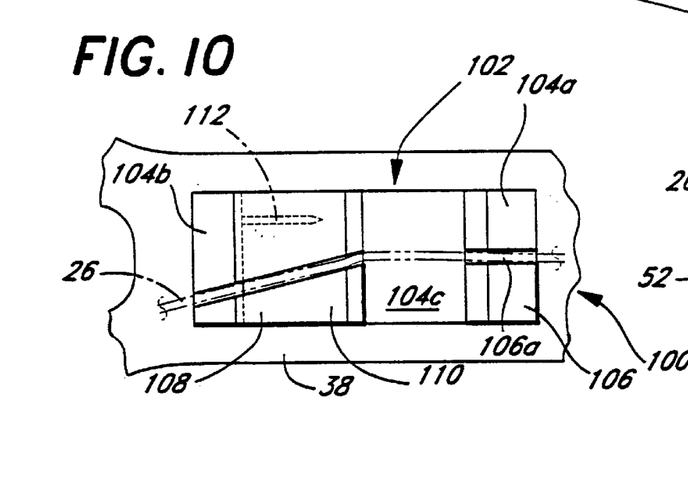
FIG. 10 is a plan view taken along line 10—10 of FIG. 9.
Figure 11:
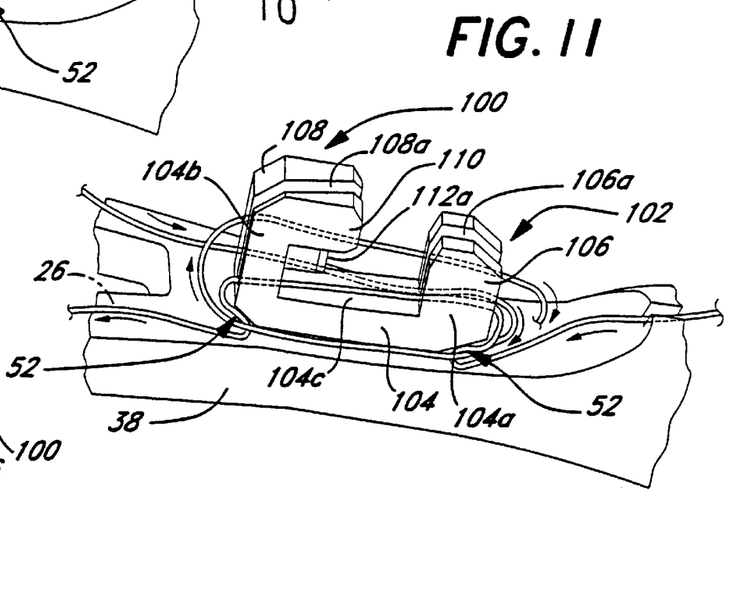
FIG. 11 is an enlarged, fragmentary perspective view of the second embodiment shown in FIG. 9 with the floss being wrapped around the post.

The post 42 is in the form of a block which is seated on the neck portion 38 in a position so that there are lands 44 and 46 on either side of the post. A guideway in the form of a Y-shaped slot 48 is cut into the top wall surface of a lower section 42a of the post 42 adjacent the passageway or slot 40. On the upper section 42b of the post 42 is a blade 50 used to sever the floss 26. As best shown in FIGS. 1c, 4 and 8, the top walls of the sections 42a and 42b converge inward towards each other with the two arms 48a and 48b of the Y-shaped slot 48 terminating at the point where these walls merge. The leg 48c of the Y-shaped slot 48 is aligned with the elongated slot 40. As best illustrated in FIGS. 3 and 8, there are notch structures 52 and 54 formed by the underside walls 52a and 54a of the post 42 intersecting with the top wall 60 of the neck portion 38. The walls 52a and 54a both slant inward towards each other.

To use the dental flosser 10 of this invention, the user grasps the end 26a of the floss 26 and guides it through the slot 40 in the cap member 16 and into the Y-shaped slot 48, either to the right or to the left of the upper section 42b. As depicted in FIG. 6, the end 26a of the floss 26 is then passed through the one opening 30c and then into the opening 30b, extending across the space between the ends 30a and 32a of the fingers 30 and 32 and into the opening 32b and then into the opening 32c. As depicted in FIGS. 7 and 8, the user then wraps the floss 26 around one section 26b of the floss 26 extending from the handle 12 to the post 42 so that this section of floss 26 is pulled into the one notch structure 56.

The user continues to wrap the floss 26 around the post 42, wedging it into the notch structures 54 and 56. Preferably, the floss 26 is wrapped two or three times around the post 42 to fasten securely the floss in position so that it is in tension across the space between the fingers. The user may then cut the end of the floss 26 using the blade 50.

The second embodiment of this invention, the dental flosser 100 shown in FIGS. 9 through 12, is similar to the first embodiment, with the main difference being the construction of the post. In the dental flosser 100 a post 102 is used which has a substantially C-shaped configuration and includes a base 104. The notch structures 52 are formed adjacent the base 104, between the base and the neck portion 38. This base 104 has a proximal end 104a and a distal end 104b with raised arms 106 and 108 at each end. Each raised arm 106 and 108 has a slot 106a and 108a therein, and the slots are offset relative to each other 106a and 108a. Specifically, the slot 108a is slanted with respect to the slot 106a. These slots 106a and 108a serve as a passageway for the dental floss 26.

The raised arm 108 at the distal end 104b of the base 104 has a lip 110 extending inward towards the proximal end 104a of the base. A straight blade 112 is seated on the post 102 and orientated lengthwise, extending between the lip 110 and the inside upper surface 104c of the base 104. The blade 112 is embedded in plastic material from which the post 102 is made. This blade 112 is positioned next to one side of the slot 108a, and it has a linear cutting edge 112a facing the proximal end 104a of the base 104 and spaced from this proximal end.

Figures 12, 13:
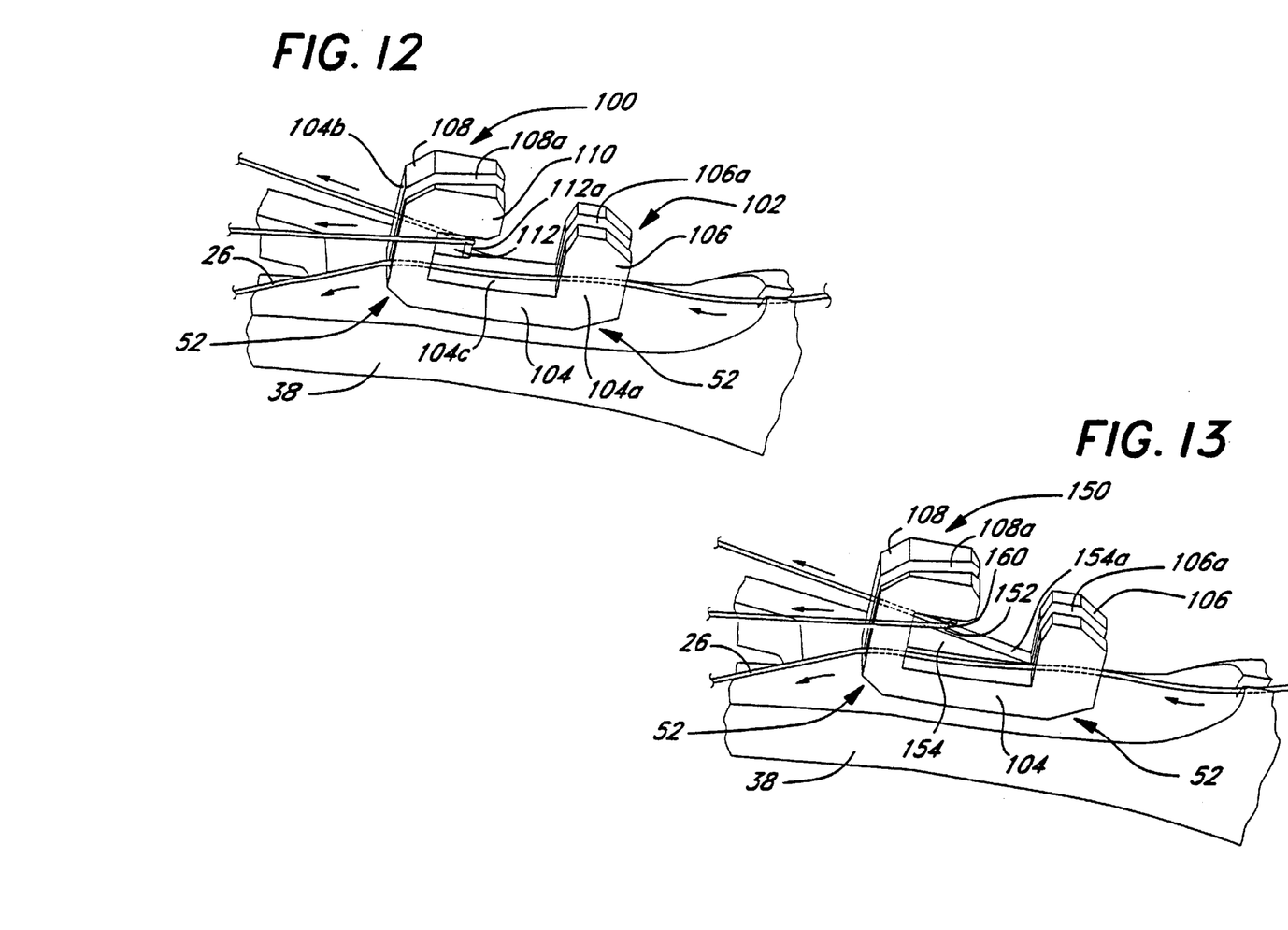
FIG. 12 is an enlarged, fragmentary perspective view of the second embodiment shown in FIG. 9 with the floss being severed.
FIG. 13 is an enlarged, fragmentary perspective view of a third embodiment of this invention.

The third embodiment of this invention, the dental flosser 150 shown in FIG. 13, is similar to the second embodiment, with the main difference being the location of a hook-type blade 152. In this embodiment there is a ramp 154 positioned on the base 104 between the raised arms 106 and 108. The ramp 154 has a slanted top surface 154a position on the base 104 with the end of the ramp near the distal end 104b of the base 104 being elevated relative to its opposite end near the proximal end 104a. A hook-type blade 160 is mounted on the top surface 154a of the ramp.

The second and third embodiments of this invention are used in a manner similar to the first embodiment by pulling the floss 26 from the handle 12, cutting the floss to the appropriate length, guiding the floss through the passageways provided by the slots 108a and 108b, threading the floss through the openings 30b and 32b in the finger elements 30 and 32, wrapping the end of the floss around the post 102, and wedging the free end of the floss in the notch structures 52.

Figure 14:
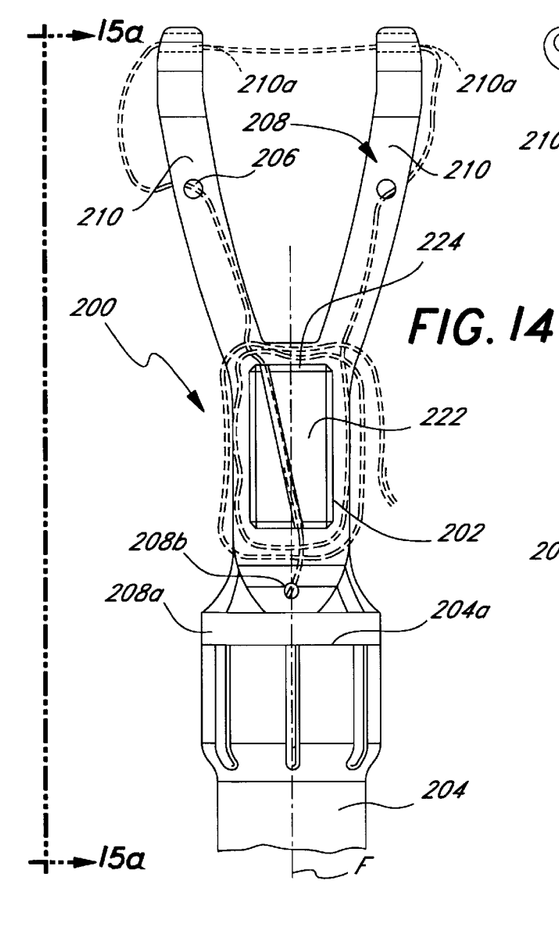
FIG. 14 is a plan view of the cap member of a fourth embodiment of the dental flosser of this invention.
Figure 15A:
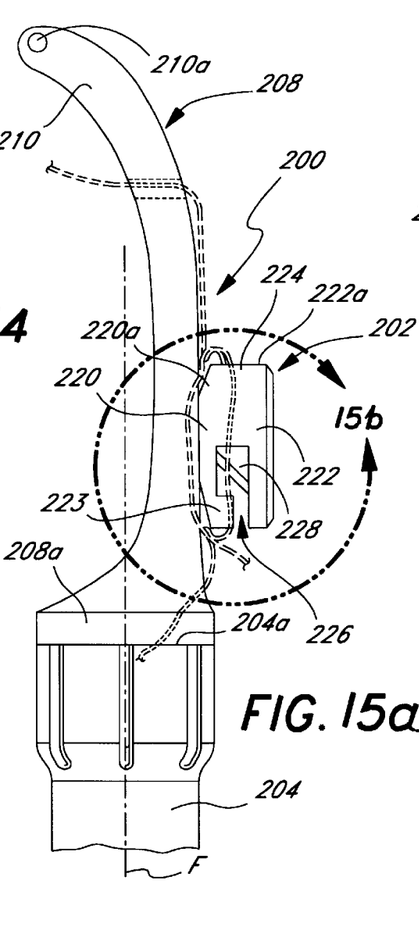
FIG. 15a is a side view of the cap member shown in FIG. 14 taken along line 15a—15a of FIG. 14.
Figure 15B:
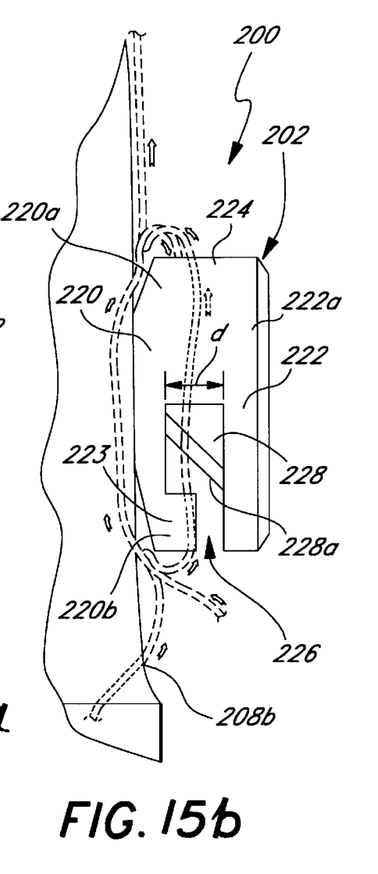
Figures 16, 17:
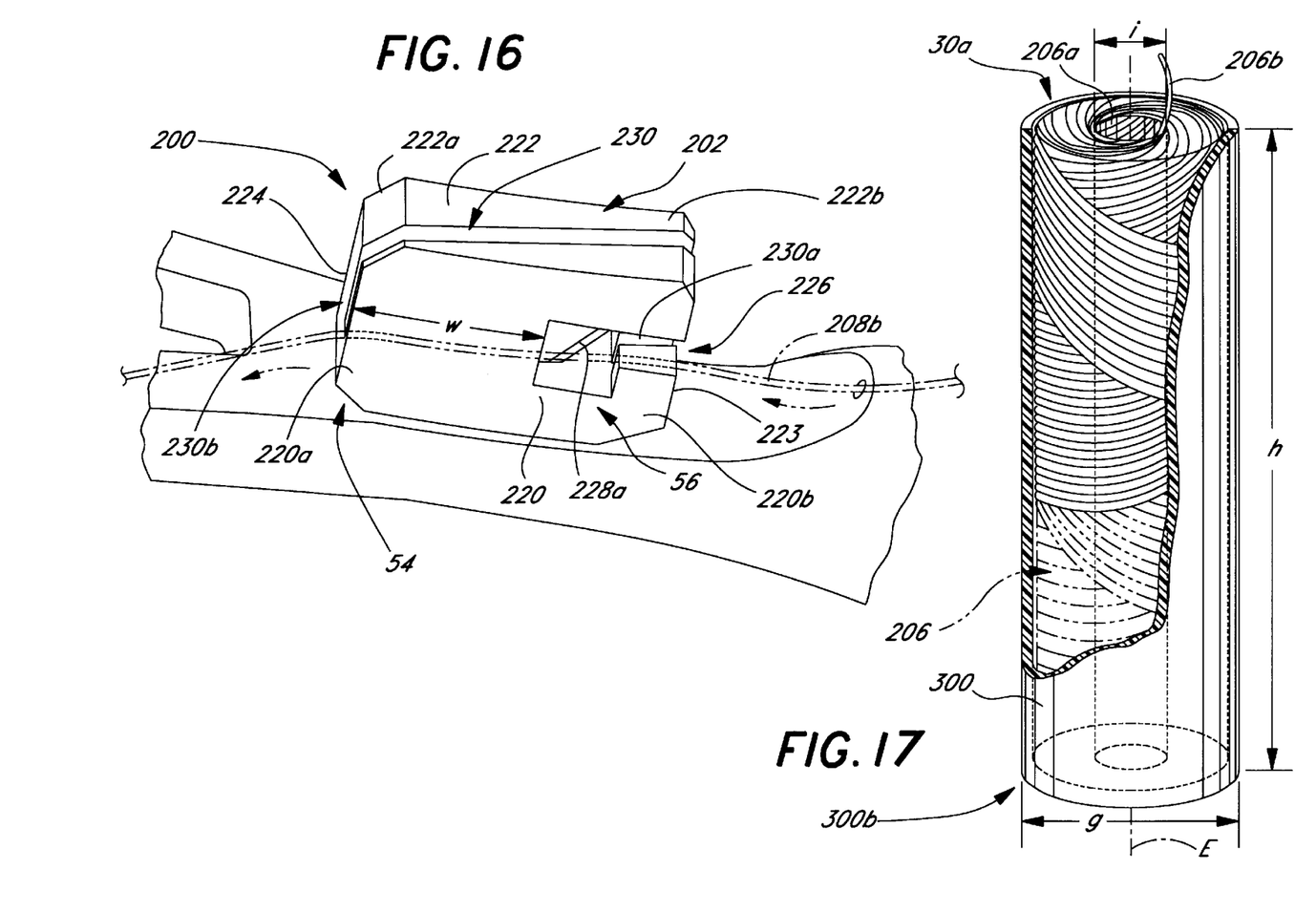
FIG. 16 is a fragmentary perspective view of the fourth embodiment of this invention showing the details of the post.
FIG. 17 is a perspective view of the preferred roll of floss used with any of the embodiments of this invention.

The fourth embodiment of this invention, the flosser 200, is shown in FIGS. 14 through 16. This flosser 200 is similar to the other embodiments, with the principal difference being the configuration of its post 202. Preferably, the post 204, like to the posts of the other embodiments, has the notch structures 54 and 56 at opposite ends thereof, enabling floss to be wrapped around the post 204 and wedged into the notch structures.

The flosser 200 includes a handle 204 having a hollow interior (not shown) which holds a supply of dental floss such as the roll 206 of floss shown in FIG. 17. The post 202 is near the handle 204, which has an open end 204a providing access to its hollow interior. The roll 206 is disposed lengthwise in this hollow interior so that the longitudinal axis E of the roll 206 is essentially co-extensive with the longitudinal axis F of the handle 204. The post 202 is attached to a cap member 208 similar to the cap members of the other embodiments, except for the configuration of the post 202. This cap member 208 has one end 208a which is connected to the open end 204a of the handle 204 and another end 204b including a pair of fingers 210 which are spaced apart in a Y or V shaped orientation. Each finger 210 has a proximal end and distal end and an opening 210a therein near the distal end thereof. The cap member 208 has a guideway 208b therein which permits an end 206b of the roll 206 floss to pass from the hollow interior of the handle 204 and be treaded through the holes 210a in the fingers 210.

The post 202 has a base 220 and a top plate 222 which are about the same length, preferably from about 0.5 inch to about 1.5 inch. The base 220 and a top plate 222 each have a forward end 220a and 222a, respectively, near the pair of fingers 210, and each have a rear end 220b and 222b, respectively, near the handle 204. The top plate 222 overlies the base 220 so that the base and top plate are substantially co-extensive along their respective lengths. Preferably, the top plate 222 and the base 220 also have the same widths, which are also co-extensive.

A connecting member 224 connects the forward ends 220a and 222a, respectively, of the base 220 and top plate 222 and spaces the base and top plate into a substantially parallel orientation with respect to each other and provides an open section 226 between the rear ends 220b and 222b, respectively, of the base and top plate. This connecting member 224 has a width w (FIG. 16) which is over 50% of the length of the base 220 and top plate 222. The distance d (FIG. 15b) between the base 220 and top plate 22 is from about 0.25 inch to about 0.5 inch. There is a lip 223 at a substantially right angle with respect to the base 220 at the open section 226. A blade 228 for cutting floss is disposed between the base 220 and the top plate 222 next to the connecting member 224 which has its cutting edge 228a at an acute angle with respect to the base 220. A slanted passageway 230 extends through the top plate 222, with a portion 230a extending into the lip 223 and another portion 230b extending into the connecting member 224.

As shown in FIG. 17, the roll 206 of floss is in the form of an elongated, cylindrically shaped roll which has a hollow, open core 206a with an end 206b of the floss extending from the open core. The end 206b passes through the guideway 208b and slanted passageway 230, including the portions 230a and 230b, and is then threaded through the fingers 210 as shown in FIG. 14. As desired, but preferably after each use, the floss wrapped around the post 204 is unwound from the notches 54 and 56 and new floss is advanced to a position between the fingers 210, wound about the notches 54 and 56, and the used floss severed by pressing it against the blade 228. The outside diameter g of the roll 206 ranges from about 10 to about 13 millimeters, the length h of the roll 206 ranges from about 50 to about 60 millimeters, and the diameter i of the hollow, open core 206a ranges from about 2 to about 4 millimeters. Preferably, the roll 206 is enclosed within a cylindrical envelope 300 made of, for example, a translucent or opaque medical tape or equivalent material. This envelope 300 is open at both its opposed ends 300a and 300b for ease of insertion of the roll 206 into the envelope. This envelope 300 provides support for the roll 206 as floss is drawn from the roll, and prevents entanglement of the last few yards of the floss as the floss is consumed.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiment disclosed. On the contrary, the intention is to cover all modifications and alternate constructions coming within the spirit and scope of the invention as generally expressed by the following claims, which particularly point out and distinctly claim the subject matter of the invention:

What is claimed is:

1. A dental flosser including
   a handle having a hollow interior adapted to hold a supply of dental floss, said handle having open end providing access to the hollow interior,
   a cap member having one end which is connected to the open end of the handle and another end including a pair of finger elements which are spaced apart, each finger element having a proximal end and distal end and an opening therein near the distal end thereof,
   said end of the cap member which is connected to the handle having a guideway therein which permits floss to pass from the hollow interior and be threaded through the openings in the fingers,
   a post near the handle which has a base of a predetermined length with a forward end near the pair of finger elements and a rear end near the handle, a top plate having a length substantially equal to the predetermined length of the base and overlying said base so that said base and top plate are substantially co-extensive along their respective lengths, said top plate having a forward end near the pair of finger elements and a rear end near the handle, and a connecting member which connects the forward ends of the base and top plate and spaces said base and top plate into substantially parallel orientation with respect to each other and provides an open section between the rear ends of the base and top plate, and
   a blade for cutting the floss disposed between the base and top plate.

2. The dental flosser of claim 1 where the post has notch structures at opposite ends thereof, enabling floss to be wrapped around the post and wedged into the notch structures.

3. The dental flosser of claim 1 where the finger elements join together at proximal ends thereof to form a fork configuration.

4. The dental flosser of claim 3 where the post is adjacent the proximal ends of the finger elements.

5. The dental flosser of claim 1 including a slanted passageway extending through said top plate.

6. The dental flosser of claim 1 where in each finger element there is an intermediate hole between the proximal and distal ends of the finger elements.

7. The dental flosser of claim 1 where the fingers are arranged in a generally V-shaped configuration.

8. The dental flosser of claim 1 where the cap member may be disconnected from the handle to allow floss to be placed in the hollow interior of the handle.

9. A dental flosser including
   a handle having a hollow interior adapted to hold a supply of dental floss, said handle having an open end providing access to the hollow interior,
   a cap member having one end which is connected to the open end of the handle and another end including a pair of finger elements which are spaced apart, each finger element having a proximal end and distal end and an opening therein near the distal end thereof,
   said end of the cap member which is connected to the handle having a guideway therein which permits floss to pass from the hollow interior and be threaded through the openings in the fingers,
   a post near the handle which has a base with notch structures at opposite ends thereof, enabling floss to be wrapped around the post and wedged into the notch structures,
   said base having a proximal end and a distal end with a raised arm at each end, said arms each having a slot therein, with said slots being offset relative to each other, said slots serving as a passageway for the floss, and
   a blade attached to the post near said distal end of the base.

10. The dental flosser of claim 9 where the blade is next to the slot in said distal end of the base and spaced from the proximal end of the base, said blade having a cutting edge facing the proximal end of the base.

11. The dental flosser of claim 10 where said raised arm at the distal end of the base has a lip extending inward towards the proximal end of the base, and the blade is seated on the post to extend between the lip and the base and to one side of the slot in the arm at the distal end of the base, with the cutting edge of the blade orientated lengthwise and extending between said base and lip.

12. The dental flosser of claim 11 where the blade is substantially straight.

13. The dental flosser of claim 12 where there is a ramp having a slanted top surface position on the base between the proximal and distal ends of the base, with a hook-type blade mounted on the top surface.

14. The dental flosser of claim 13 where the ramp has a distal end and a proximal end with the distal end being elevated relative to the proximal end.

15. The dental flosser of claim 13 where the post has a substantially C-shaped configuration.

16. A dental flosser including:
   a handle having a hollow interior adapted to hold a supply of dental floss, said handle having open end providing access to the hollow interior,
   a cap member having one end which is connected to the open end of the handle and another end including a pair of finger elements which are spaced apart, each finger element having a proximal end and distal end and a hole therein near the distal end thereof,
   said end of the cap member which is connected to the handle having a passageway therein which permits floss to pass from the hollow interior and be threaded through the holes in the fingers,
   a post near the handle which has notch structures at opposite ends thereof, enabling floss to be wrapped around the post and wedged into the notch structures,
   said post having a guideway thereon for guiding the floss, said guideway having a generally Y-shaped configuration, and
   a blade on the cap member for cutting the floss.

17. A dental flosser including
   a handle having a hollow interior adapted to hold a supply of dental floss, said handle having an open end providing access to the hollow interior,
   a cap member having one end which is connected to the open end of the handle and another end including a pair of finger elements which are spaced apart, each finger element having a hole therein near a distal end thereof, said end of the cap member which is connected to the handle having a passageway therein which permits floss to pass from the hollow interior and be threaded through the holes in the fingers, a post attached to the cap member between the fingers elements and said one end of the cap member, said post including a guideway for the floss having a generally Y-shaped configuration and a blade member for cutting the floss, said post having an underside which intersects the cap member at an acute angle to provide a notch structure.

18. The dental flosser of claim 17 where the cap member is removeable from the handle to allow floss to be placed in the hollow interior of the handle.

19. A dental flosser including:

a handle having a hollow interior which holds a supply of dental floss, said handle having an open end providing access to the hollow interior so that the handle may be refilled with a supply of dental floss as needed, a cap member removably attached to the handle at the open end of the handle, so that upon removal of the cap member access to the interior is provided, said cap member having one end which is connected to the open end of the handle and another end including first and second finger elements which are spaced apart, each finger element having a proximal end and distal end, with the proximal ends of the finger elements merging together at a common junction, a first hole in each of the finger elements near the distal ends thereof, each hole being aligned with each other, enabling the floss to be stretched across the space between the distal ends of the finger elements, a second hole in each of the finger elements at an intermediate portion of the finger elements, said floss first passing through an intermediate hole in the first finger element, next passing through the first hole in said first finger element, then stretching across said space and passing through the first hole in the second finger element, and then passing through the second hole in said second finger element, a passageway in the handle which permits floss to pass from the hollow interior and be threaded through the holes in the fingers, a post on the cap member between said junction and the handle, said post having a notch structure which enables the floss after passing through said holes in the finger elements to be wrapped around the post and wedged into the notch structure to hold the floss firmly in position during use of the flosser and a guideway for the floss having a generally Y-shaped configuration, and a blade on the cap member for cutting the floss.

20. The dental flosser of claim 19 where the notch structure is on the underside of the post and includes a pair of spaced apart wall elements, each converging towards each other to intersect the cap member at an acute angle.

* * * * *